(12) United States Patent
Blanchard et al.

(10) Patent No.: US 12,364,421 B2
(45) Date of Patent: Jul. 22, 2025

(54) INTRAVENOUS CATHETER DEVICE HAVING A PROBE ASSEMBLY WITH AN INTEGRATED FLUID FLUSHING MECHANISM

(71) Applicant: Becton, Dickinson and Company, Franklin Lakes, NJ (US)

(72) Inventors: Curtis H. Blanchard, Riverton, UT (US); Jonathan Karl Burkholz, Salt Lake City, UT (US); Megan Scherich, Salt Lake City, UT (US); Weston F. Harding, Lehi, UT (US); Yiping Ma, Layton, UT (US); Benjamin Hopwood, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 356 days.

(21) Appl. No.: 17/496,292

(22) Filed: Oct. 7, 2021

(65) Prior Publication Data
US 2022/0110561 A1  Apr. 14, 2022

Related U.S. Application Data

(60) Provisional application No. 63/089,417, filed on Oct. 8, 2020.

(51) Int. Cl.
*A61B 5/15* (2006.01)
*A61M 5/14* (2006.01)

(52) U.S. Cl.
CPC .... *A61B 5/150992* (2013.01); *A61B 5/15003* (2013.01); *A61M 2005/1403* (2013.01)

(58) Field of Classification Search
None
See application file for complete search history.

(56) References Cited

U.S. PATENT DOCUMENTS

| 4,492,634 | A | 1/1985 | Villa-Real |
| 4,894,052 | A | 1/1990 | Crawford |
| 5,156,596 | A | 10/1992 | Balbierz et al. |
| 5,873,841 | A | 2/1999 | Brannon |
| 6,923,184 | B1 * | 8/2005 | Russo ............... A61M 16/0463 |
| | | | 128/207.14 |
| 7,713,256 | B2 | 5/2010 | Brimhall et al. |
| 8,690,833 | B2 | 4/2014 | Belson |
| 2003/0055381 | A1 | 3/2003 | Wilkinson |

(Continued)

FOREIGN PATENT DOCUMENTS

| CN | 110141255 A | 8/2019 |
| EP | 1293162 A2 | 3/2003 |

(Continued)

*Primary Examiner* — Daniel L Cerioni
*Assistant Examiner* — Om Patel
(74) *Attorney, Agent, or Firm* — The Webb Law Firm

(57) ABSTRACT

An IV catheter device can include or being configured to employ a probe assembly having an integrated fluid flushing mechanism. The probe assembly can be configured in a variety of ways to cause flushing fluid to be injected through a fluid permeable structure of the probe as the probe is advanced distally from a catheter. In this way, the fluid permeable structure can be kept clear of any occlusion that may otherwise form. With the probe extending distally from the catheter, a blood sample may be collected.

12 Claims, 15 Drawing Sheets

(56) References Cited

U.S. PATENT DOCUMENTS

| | | |
|---|---|---|
| 2003/0135237 A1 | 7/2003 | Cragg et al. |
| 2005/0074363 A1* | 4/2005 | Dunfee ............... G01N 35/1079 422/81 |
| 2006/0161115 A1 | 7/2006 | Fangrow |
| 2006/0247582 A1* | 11/2006 | Alheidt ............ A61M 25/10182 604/228 |
| 2008/0312576 A1 | 12/2008 | McKinnon et al. |
| 2009/0259201 A1 | 10/2009 | Hwang et al. |
| 2010/0113971 A1* | 5/2010 | Hibner ............... A61B 10/0275 600/564 |
| 2011/0009717 A1 | 1/2011 | Davis et al. |
| 2014/0042094 A1 | 2/2014 | Montagu et al. |
| 2014/0171821 A1* | 6/2014 | Govari ................. A61B 5/0036 600/549 |
| 2015/0025348 A1 | 1/2015 | Grabowski |
| 2016/0317783 A1* | 11/2016 | Vincent ................ A61M 39/26 |
| 2016/0324455 A1 | 11/2016 | Crosby et al. |
| 2018/0140240 A1 | 5/2018 | Bullington et al. |
| 2018/0263647 A1* | 9/2018 | Aljuri ...................... A61B 8/12 |
| 2019/0021640 A1 | 1/2019 | Burkholz et al. |
| 2019/0236956 A1 | 8/2019 | Uchimura et al. |
| 2019/0321599 A1 | 10/2019 | Burkholz et al. |
| 2019/0374144 A1 | 12/2019 | Langdell et al. |
| 2020/0170559 A1 | 6/2020 | Burkholz et al. |
| 2020/0369443 A1* | 11/2020 | Heinbuch ............ B67D 7/0277 |
| 2021/0228127 A1 | 7/2021 | Burkholz et al. |

FOREIGN PATENT DOCUMENTS

| | | |
|---|---|---|
| EP | 3207970 A1 | 8/2017 |
| WO | 9213584 A1 | 8/1992 |
| WO | 9834532 A1 | 8/1998 |
| WO | 2004032995 A2 | 4/2004 |
| WO | 2013028759 A1 | 2/2013 |
| WO | 2019236956 A2 | 12/2019 |

* cited by examiner

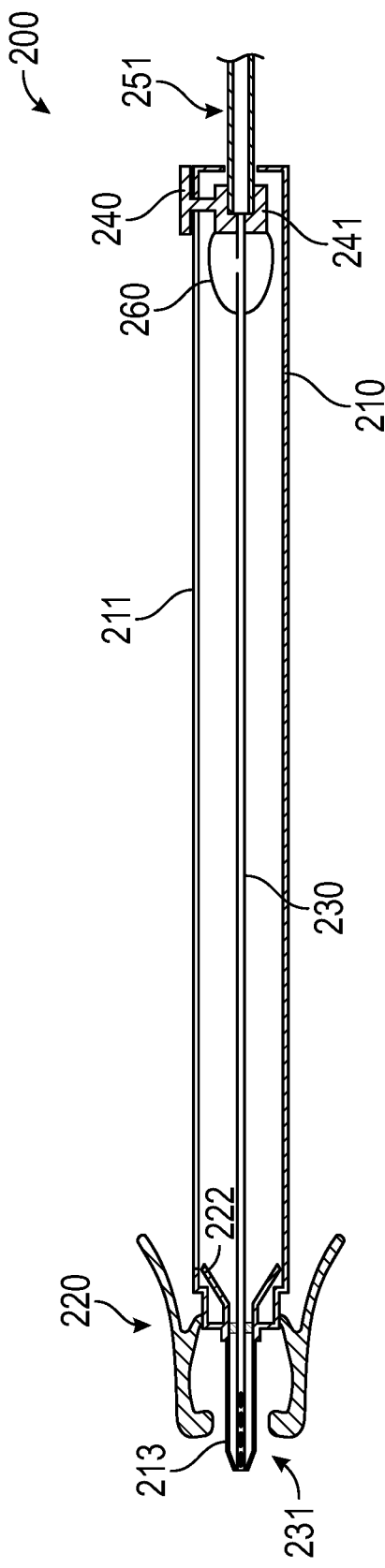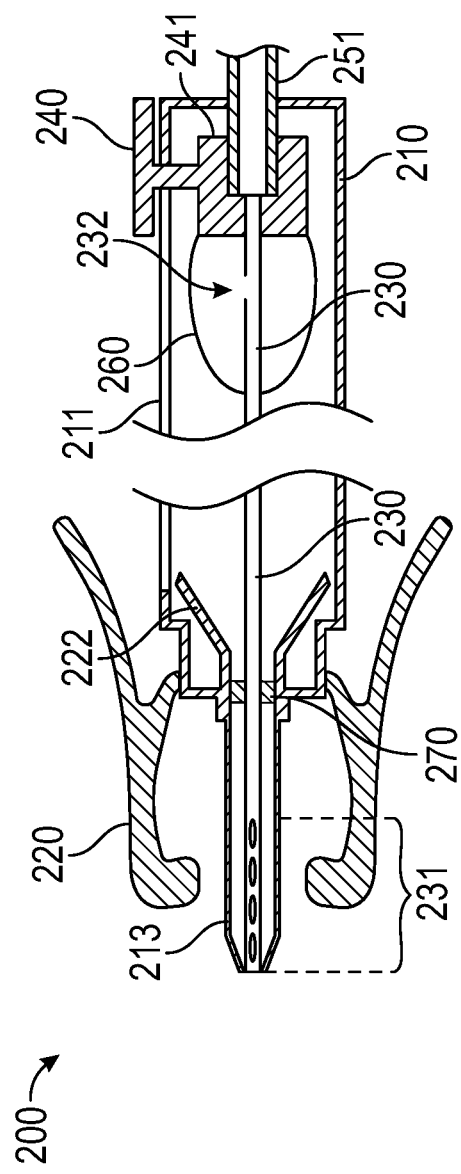
FIG. 2
FIG. 2A

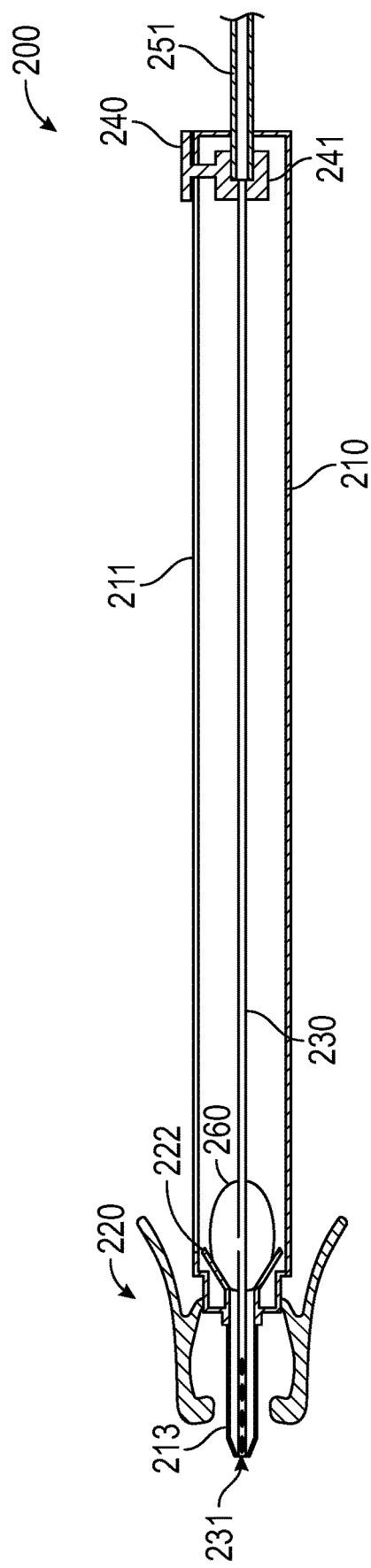
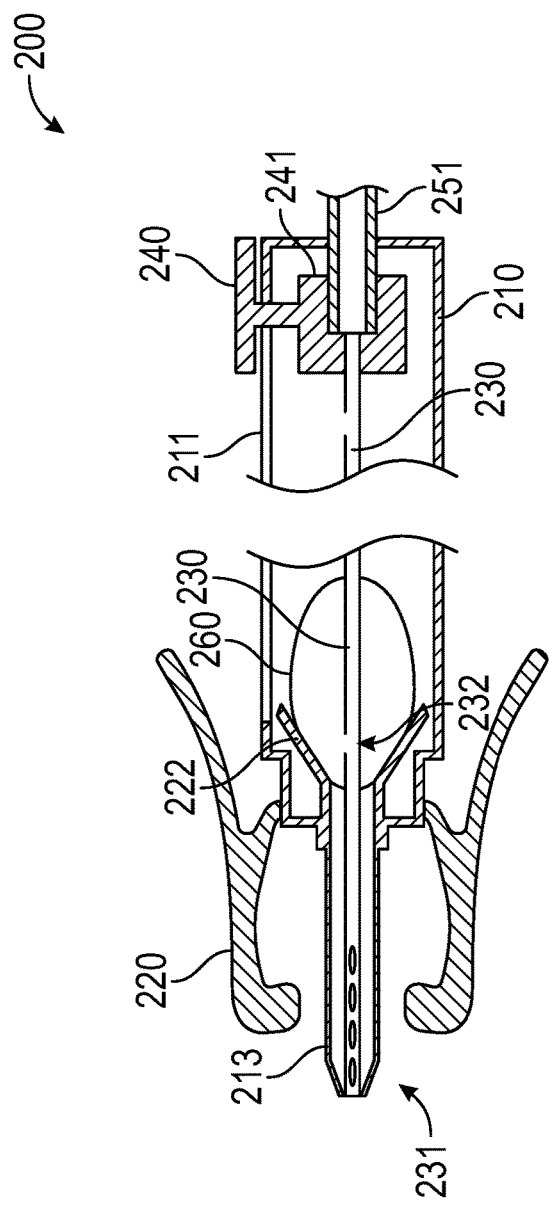
FIG. 4
FIG. 4A

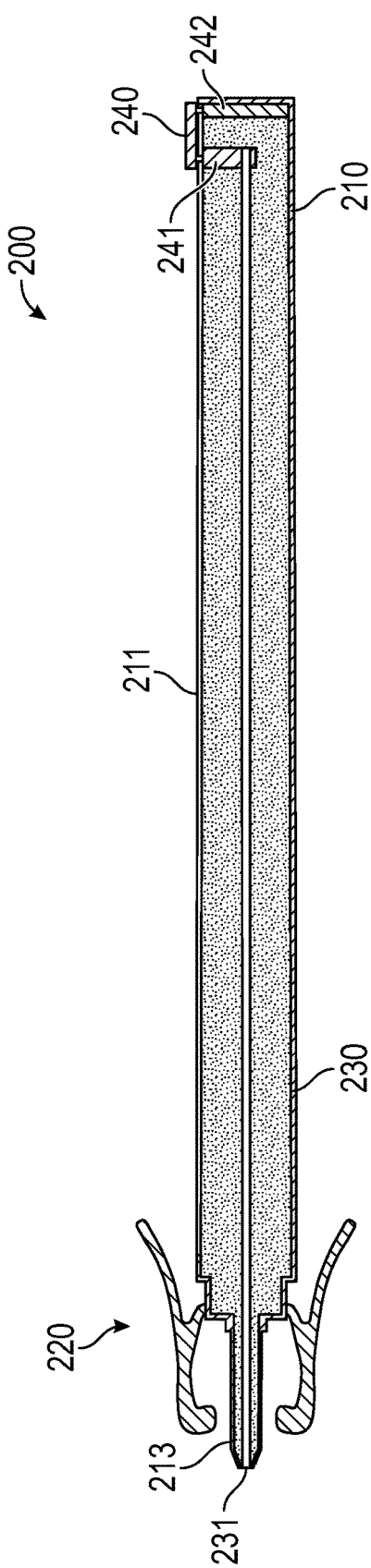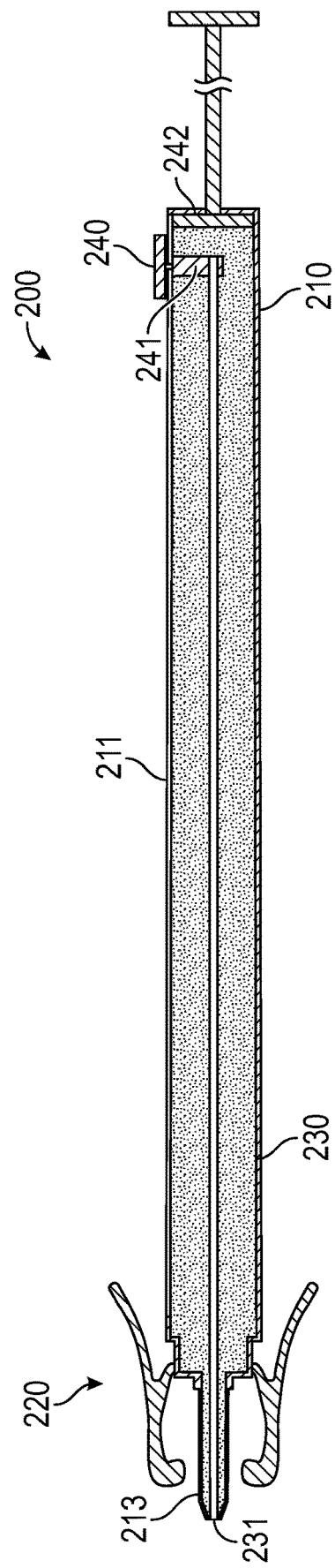
FIG. 5
FIG. 6

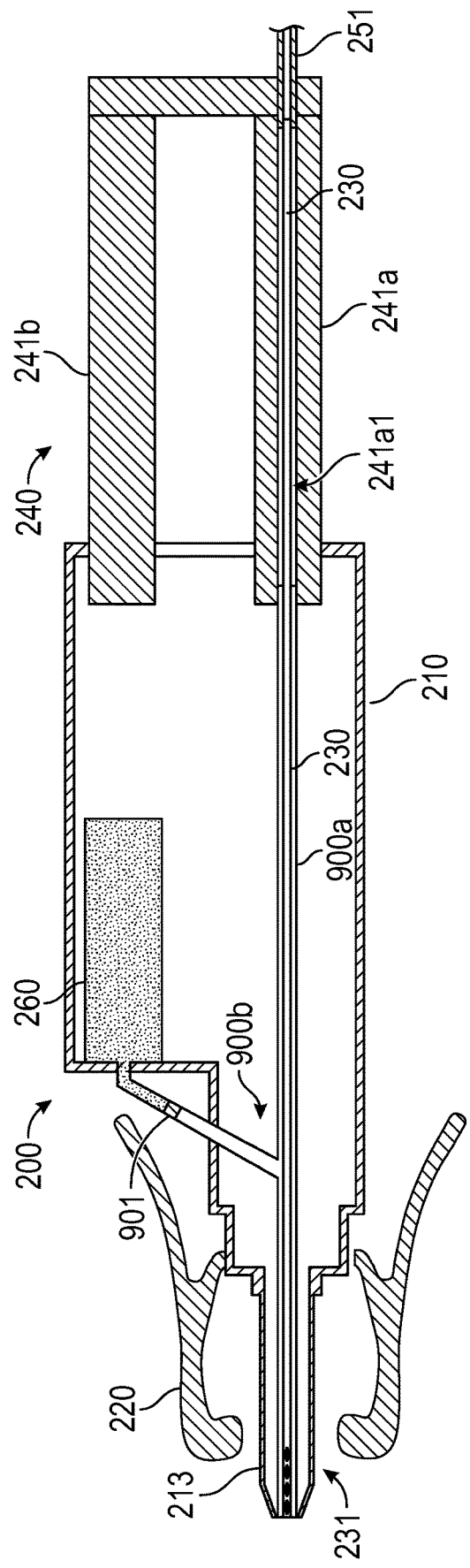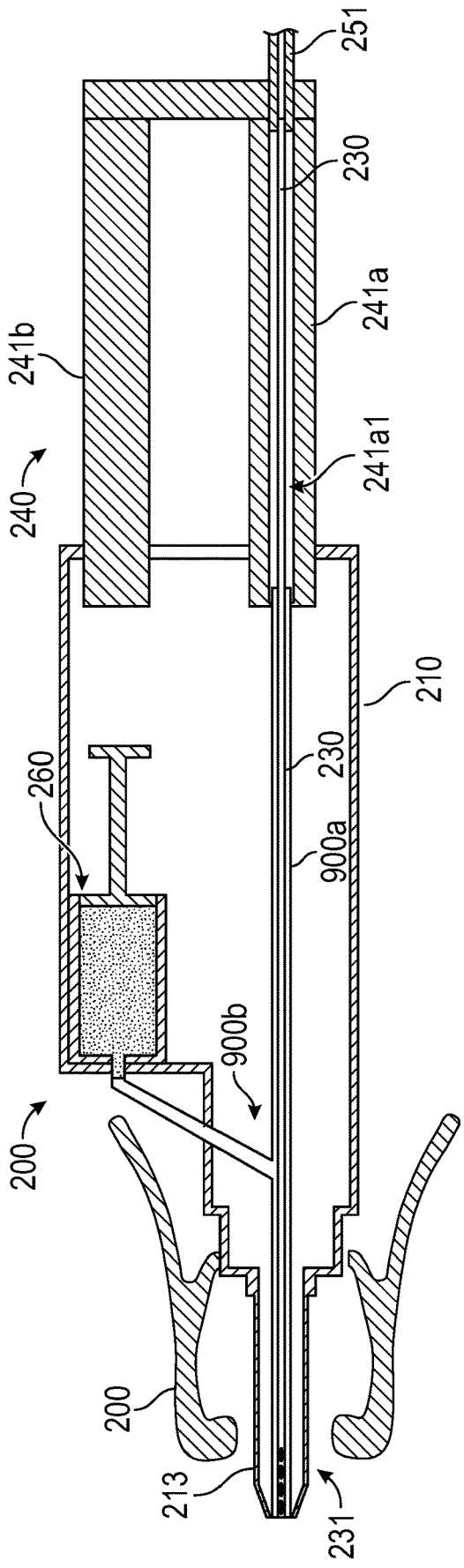
FIG. 9
FIG. 10

INTRAVENOUS CATHETER DEVICE HAVING A PROBE ASSEMBLY WITH AN INTEGRATED FLUID FLUSHING MECHANISM

CROSS-REFERENCE TO RELATED APPLICATION

The present application claims priority to U.S. Provisional Application Ser. No. 63/089,417, entitled "Intravenous Catheter Device Having a Probe Assembly with an Integrated Fluid Flushing Mechanism", filed Oct. 8, 2020, the entire disclosure of which is hereby incorporated by reference in its entirety.

BACKGROUND

Intravenous (IV) catheter devices are commonly used for a variety of infusion therapies. For example, an IV catheter device may be used for infusing fluids, such as normal saline solution, various medicaments, and total parenteral nutrition, into a patient. IV catheter devices may also be used for withdrawing blood from the patient.

A common type of IV catheter device is an over-the-needle peripheral intravenous ("IV") catheter ("PIVC"). As its name implies, the over-the-needle catheter may be mounted over a needle having a sharp distal tip. The catheter and the needle may be assembled so that the distal tip of the needle extends beyond the distal tip of the catheter with the bevel of the needle facing up away from skin of the patient. The catheter and needle are generally inserted at a shallow angle through the skin into the vasculature of the patient. Once the catheter is positioned within the vasculature, it may become occluded such as when a thrombus forms around the catheter's distal opening or the distal opening is positioned against a vessel wall.

When IV catheter devices are maintained within the patient's vasculature, they are likely to become occluded. Once an IV catheter device is occluded, it may no longer be possible to use the IV catheter device to infuse fluids or withdraw blood. In such cases, the IV catheter device may be replaced. Yet, replacing an IV catheter device is burdensome for the patient and increases costs. To address such issues, some devices have been developed that can be inserted through the indwelling catheter of the IV catheter device to remove the occlusion. For example, some devices employ rigid tubing that can be inserted through the catheter and distally beyond the catheter's distal opening. With the rigid tubing inserted in this manner, such devices can obtain a blood sample through the rigid tubing even if the catheter had become occluded. In other words, the rigid tubing is employed to physically pass through any occlusion that may have formed in or around the catheter's distal opening and forms a separate fluid pathway from the catheter for collecting the blood sample.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to an IV catheter device that has a probe assembly with an integrated fluid flushing mechanism. The probe assembly can be configured in a variety of ways to cause flushing fluid to be injected through a fluid permeable structure of the probe as the probe is advanced distally from a catheter. In this way, the fluid permeable structure can be kept clear of any occlusion that may otherwise form. With the probe extending distally from the catheter, a blood sample may be collected.

In some embodiments, a probe assembly may include a probe housing and a probe that extends within the housing. The probe may have a fluid permeable structure at a distal end of the probe. The probe assembly may also include a probe actuator that is configured to advance the probe from a proximal position to a distal position. The probe assembly may further include an integrated fluid flushing mechanism that is configured to cause a flushing fluid to flow through the fluid permeable structure as the probe is advanced to the distal position.

In some embodiments, the probe assembly may be configured to couple to a catheter adapter from which a catheter extends. In such cases, when the probe is advanced to the distal position, the fluid permeable structure may extend at least partially through a distal end of the catheter.

In some embodiments, the integrated fluid flushing mechanism may include a fluid container. In some embodiments, the fluid container may be compressed as the probe is moved into the distal position. In some embodiments, the fluid container may be compressed between the probe actuator and a compressing structure. In some embodiments, the fluid container may be a syringe. In some embodiments, the syringe may be positioned within the probe housing or may be positioned external to the probe housing.

In some embodiments, the probe assembly may further include a probe tube within which the probe extends and a probe tube branch that connects the probe tune to the fluid container. In some embodiments, the fluid container may be formed within the probe actuator and the probe assembly may further include a valve that retains the flushing fluid within the fluid container and a valve actuator that opens the valve when the probe is moved into the distal position.

In some embodiments, the probe assembly may further include extension tubing that is fluidly coupled to the probe. In such cases, the fluid container may comprise a portion of the extension tubing that is compressed by the probe housing as the probe is moved into the distal position.

In some embodiments, the integrated fluid flushing mechanism may be a stopper. In such embodiments, the stopper may be coupled to the probe actuator or coupled to a plunger.

In some embodiments, an IV catheter device may include a catheter adapter from which a catheter extends distally and a probe assembly that is configured to couple to the catheter adapter. The probe assembly may include: a probe housing; a probe that extends within the housing, the probe having a fluid permeable structure at a distal end of the probe; a probe actuator that is configured to advance the probe from a proximal position to a distal position in which the fluid permeable structure extends distally from the catheter when the probe assembly is coupled to the catheter adapter; and an integrated fluid flushing mechanism that is configured to cause a flushing fluid to flow through the fluid permeable structure as the probe is advanced to the distal position.

In some embodiments of the IV catheter device, the integrated fluid flushing mechanism may be a fluid container. In some embodiments of the IV catheter device, the fluid container is compressed as the probe is advanced to the distal position. In some embodiments of the IV catheter device, the integrated fluid flushing mechanism may be a stopper that causes the flushing fluid to flow out from the probe housing.

In some embodiments, a method for accessing a vasculature may include: coupling a probe assembly to a catheter adapter having a catheter that is inserted into a patient's vasculature, the probe assembly comprising a probe housing, a probe that extends within the housing, a probe actuator and an integrated fluid flushing mechanism; and in conjunction with sliding the probe actuator in a distal direction to cause a fluid permeable structure of the probe to extend distally from the catheter, activating the integrated fluid flushing mechanism to thereby cause a flushing fluid to flow through the fluid permeable structure as the fluid permeable structure advances distally from the catheter. In some embodiments, the method may also include obtaining a blood sample via the probe assembly while the fluid permeable structure is advanced distally from the catheter.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which:

FIG. 2 is a cross-sectional view of a probe assembly that is configured in accordance with one or more embodiments;

FIG. 2A is a detailed cross-sectional view of the probe assembly of FIG. 2;

FIG. 4 is a cross-sectional view of a probe assembly that is configured in accordance with one or more embodiments;

FIG. 4A is a detailed cross-sectional view of the probe assembly of FIG. 4;

FIG. 5 is a cross-sectional view of a probe assembly that is configured in accordance with one or more embodiments;

FIG. 6 is a cross-sectional view of a probe assembly that is configured in accordance with one or more embodiments;

FIG. 9 is a cross-sectional view of a probe assembly that is configured in accordance with one or more embodiments;

FIG. 10 is a cross-sectional view of a probe assembly that is configured in accordance with one or more embodiments;

DESCRIPTION OF EMBODIMENTS

An IV catheter device that may be employed in some embodiments may include a catheter adapter from which a catheter distally extends and one or more ports or connectors for attaching other devices to the catheter adapter. Such devices may be attached to the catheter adapter before, during or after insertion of the catheter into a patient's vasculature and can include a needle assembly, a blood collection set, an infusion assembly, any embodiment of a probe assembly described herein, etc. Accordingly, embodiments of the present disclosure should not be limited to any particular configuration of an IV catheter device or to the specific examples of IV catheter devices used herein.

Figure 1A:
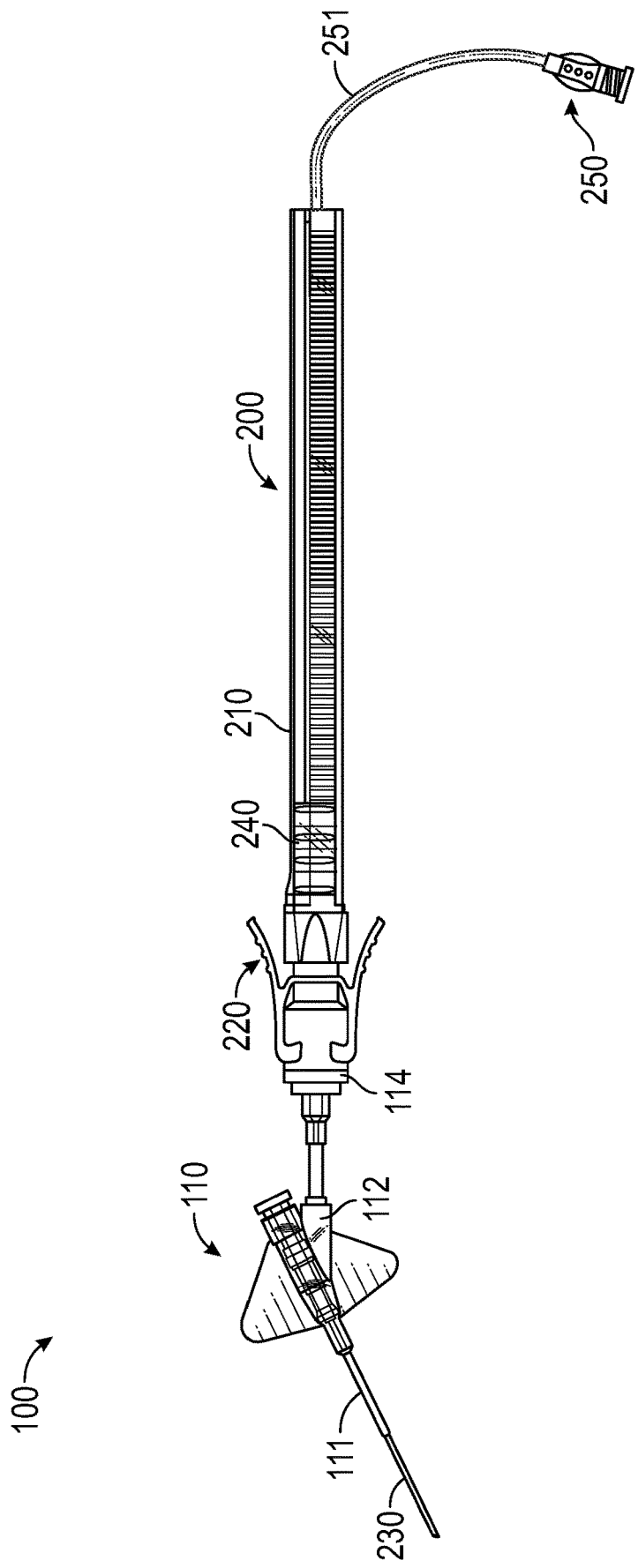
FIG. 1A illustrates one example of an IV catheter device that includes a probe assembly in accordance with one or more embodiments.
Figure 1B:
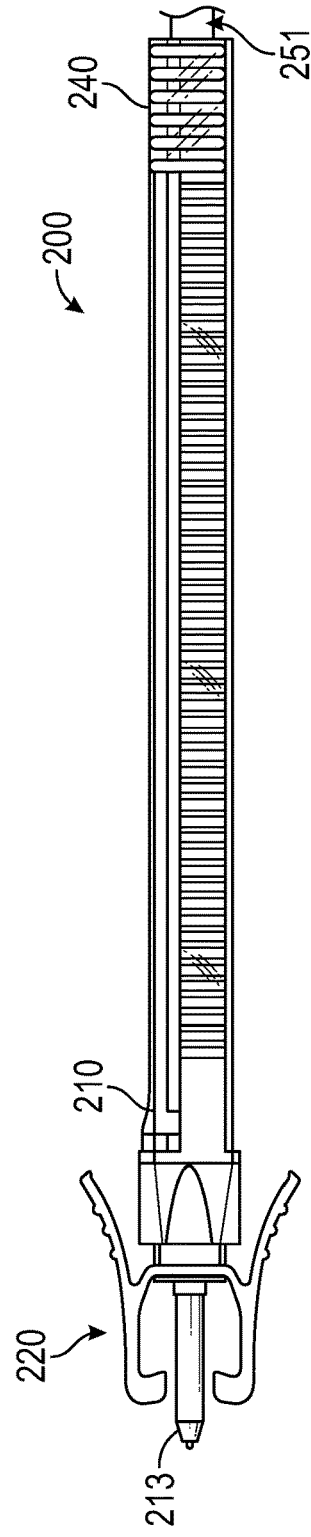
FIG. 1B illustrates the probe assembly of FIG. 1A when the probe is not extended.
Figure 1C:
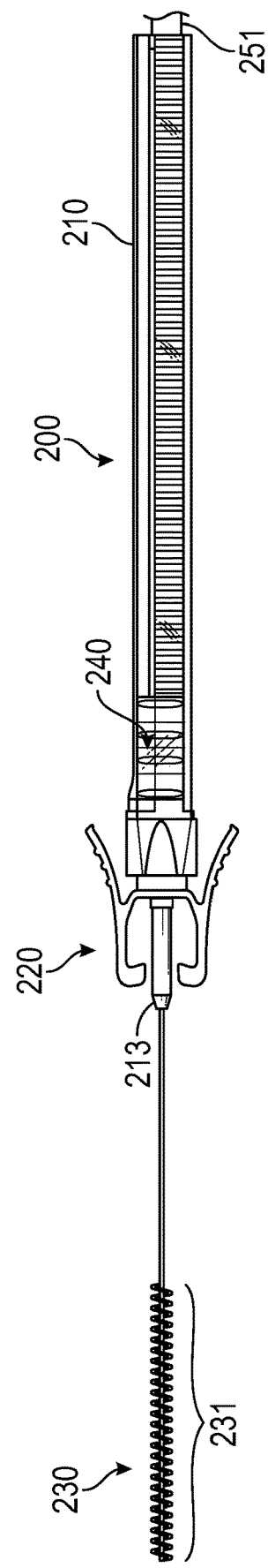
FIG. 1C illustrates the probe assembly of FIG. 1B when the probe is extended.

FIGS. 1A-1C provide an example of an IV catheter device 100 that is configured in accordance with some embodiments of the present disclosure. IV catheter device 100 includes a catheter adapter 110 from which a catheter 111 extends distally. Although not shown, a needle assembly may oftentimes be secured to catheter adapter 110 and may be employed to insert catheter 111 into a patient's vasculature and subsequently detached from catheter adapter 110. IV catheter device 110 also includes an adapter 114 that is connected to a side port 112 of catheter adapter 110.

IV catheter device 100 also includes a probe assembly 200 having a probe housing 210 which can house a probe 230 at least when probe 230 is not extended through catheter 111. A connector 220 can be formed at a distal end of probe housing 210 and can function to connect probe assembly 200 to IV catheter device 100 (e.g., via adapter 114 as shown in FIG. 1A). In other embodiments, however, probe housing 210 may be integrated into adapter 114 or another component of catheter adapter 110. In other words, how a probe assembly is connected to a catheter adapter is not essential to embodiments of the present disclosure.

Probe assembly 200 may also include a probe actuator 240 that extends out from probe housing 210 and slides along a channel 211 formed in probe housing 210. Probe actuator 240 allows a clinician to move probe 230 relative to catheter 111 by sliding probe actuator 240 along the length of probe housing 210 within channel 211. As described in detail below, a probe assembly configured in accordance with embodiments of the present disclosure may include an integrated fluid flushing mechanism that causes fluid to be injected through and/or around the distal end of probe 230 when probe actuator 240 is slide in a distal direction relative to probe housing 210.

Probe assembly 200 may further include an access port 250 that is connected to a proximal end of probe housing 210 via extension tubing 251. Access port 250 may be employed to connect a blood collection set, a fluid delivery device (e.g., a syringe) or another device to probe assembly 200.

FIGS. 1B and 1C illustrate probe assembly 200 in isolation. In FIG. 1B, probe actuator 240 is at a proximal-most position and therefore the distal end of probe 230 is positioned within distal end 213 of probe housing 210. In contrast, in FIG. 1C, probe actuator 240 is at a distal-most position which has caused probe 230 to be advanced distally out from distal end 213 and corresponds with the position of probe 230 represented in FIG. 1A. A length of probe 230 and/or the configuration of probe actuator 240 can cause the distal end of probe 230 to be positioned proximate to (e.g., proximal to, at or distal to) the distal opening of catheter 111 (or the distal opening of the catheter of any other IV catheter device with which probe assembly 200 is compatible). For example, FIG. 1A illustrates an embodiment where probe 230 extends out through the distal opening of catheter 111 when probe actuator 240 is moved to the distal-most position.

With reference to FIG. 1C, a distal end of probe 230 can include or form a fluid permeable structure 231. In the depicted example, fluid permeable structure 231 is in the form of a coil that surrounds the straight portion (i.e., un-coiled center portion) of probe 230 and allows blood or fluid to flow into catheter 111 between the straight and coiled portions. However, many other configurations of fluid permeable structure 231 could be employed. The term "fluid permeable structure" should therefore be construed as a distal portion of a probe that is configured to allow fluid to flow into a catheter when the probe extends distally through a distal end of the catheter. A probe with a fluid permeable structure would therefore encompass a guidewire that has a coil or other structure positioned around it to create a fluid pathway along the guidewire, a tube that has one or more openings at and/or along its distal end that allow fluid to flow into or out from the lumen of the tube, a tube that has a coil or other structure positioned around it to create a fluid pathway along the exterior of the tube (possibly in addition to a fluid pathway in the lumen of the tube), etc.

A probe having a fluid permeable structure may be used to remove an occlusion that may have formed around the distal opening of catheter and/or to reposition the catheter when its distal opening may be occluded by a vessel wall or other vasculature structure. For example, after inserting catheter 111 into the patient's vasculature but prior to advancing probe 230 through catheter 111, a thrombus could form around catheter 111's opening and prevent blood or fluid from flowing through catheter 111. In such a case, probe actuator 240 could be moved into the distal-most position to advance probe 230, and particularly fluid permeable structure 231, distally out through the distal opening of catheter 111. The advancement of probe 230 through the distal opening would remove any occlusion that may have formed. Also, fluid permeable structure 231 would allow blood to be collected or fluid to be injected while probe 230 is positioned in and extends distally out through catheter 111's distal opening.

Even though the advancement of probe 230 from the distal opening of catheter 111 may remove an occlusion from the distal opening, there is still a risk that an occlusion may be formed around fluid permeable structure 231 or otherwise block the flow of fluid through fluid permeable structure 231. For example, it is possible that, as probe 230 is being advanced into a desired position, a thrombus may form around fluid permeable structure 231 before reaching the desired position. In such cases, the purpose of probe 230 may have been thwarted.

In accordance with embodiments of the present disclosure, a probe assembly may be configured with an integrated fluid flushing mechanism that can minimize the likelihood that a fluid permeable structure of the probe will become occluded while the probe is being advanced distally from the catheter. For example, a fluid flushing mechanism may be integrated into probe assembly 200 and can be configured to inject fluid through catheter 111 as probe actuator 240 is moved from the proximal-most to the distal-most position. FIGS. 2-13 provide a number of examples of fluid flushing mechanisms that may be integrated into a probe assembly in accordance with embodiments of the present disclosure.

FIG. 2 is a cross-sectional side view of an embodiment of probe assembly 200 that includes an integrated fluid flushing mechanism, while FIG. 2A is a detailed view of proximal and distal portions of probe assembly 200. In FIGS. 2 and 2A, probe actuator 240 and probe 230 are shown in a proximal-most position in which the distal end of probe 230 is withdrawn into distal end 213 of probe housing 210. In contrast to FIGS. 1A-1C, in FIGS. 2 and 2A, probe 230 is in the form of a tube and has a fluid permeable structure 231 formed by a number of openings along the distal end of the tube. As stated above, this is only one of many possible configurations of a probe having a fluid permeable structure which could be employed in embodiments of the present disclosure.

Figure 13:
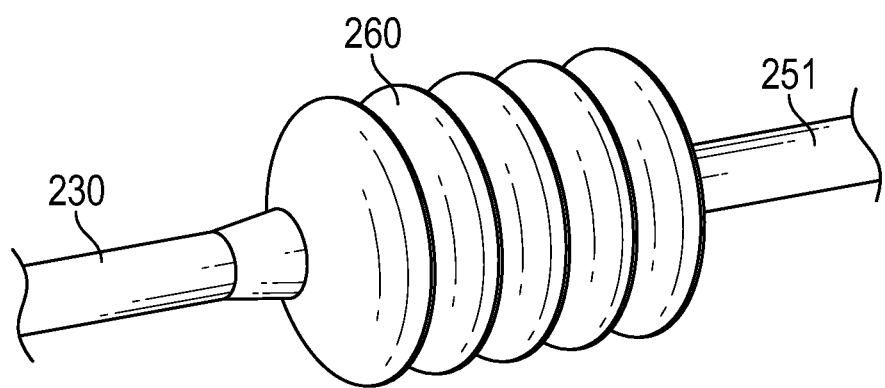
FIG. 13 is an example of a fluid container that may be used in a probe assembly that is configured in accordance with one or more embodiments.

Probe actuator 240 includes an actuator body 241 that is positioned within probe housing 210. A proximal end of probe 230 is coupled to actuator body 241. A distal end of extension tubing 251 is also coupled to actuator body 241 and is in fluid communication with the proximal end of probe 230. A fluid container 260 is positioned around probe 230 immediately adjacent to the distal side of actuator body 241. In some embodiments, fluid container 260 may be connected to actuator body 241. The portion of probe 230 that is within fluid container 260 (or that may be coupled to fluid container 260) may include an opening 232 which allows fluid within fluid container 260 to flow into probe 230 when fluid container 260 is compressed. In some embodiments, fluid container 260 may also be filled with fluid via opening 232. In other embodiments, however, fluid container 260 may be pre-filled or may be filled via another opening (e.g., via extension tubing 251). In some embodiments, fluid container 260 may be in the form of a bellows as shown in FIG. 13. In some embodiments, an air permeable membrane 270 may be positioned around probe 230 to allow air to escape from within actuator body 241 when fluid container 260 is filled. Membrane 270 may provide sufficient back pressure to cause fluid container 260 to inflate as described below. In some embodiments, a septum or valve (not shown) may be positioned within probe 230 to facilitate filling fluid container 260.

A compressing structure 222 is formed within probe housing 210 towards distal end 213. Compressing structure 222 can be configured to compress fluid container 260 as probe actuator 240 is moved towards the distal-most position. In the embodiment shown in FIGS. 2 and 2A, compressing structure 222 is in the form of outwardly angled surfaces. Accordingly, as probe actuator 240 is moved distally, fluid container 260 will insert between these outwardly angled surfaces and be compressed between the outwardly angled surfaces and actuator body 241. As fluid container 260 is compressed, the fluid contained therein will be expelled through opening 232, into the lumen of probe 230 and ultimately out through fluid permeable structure 231.

Figure 3A:
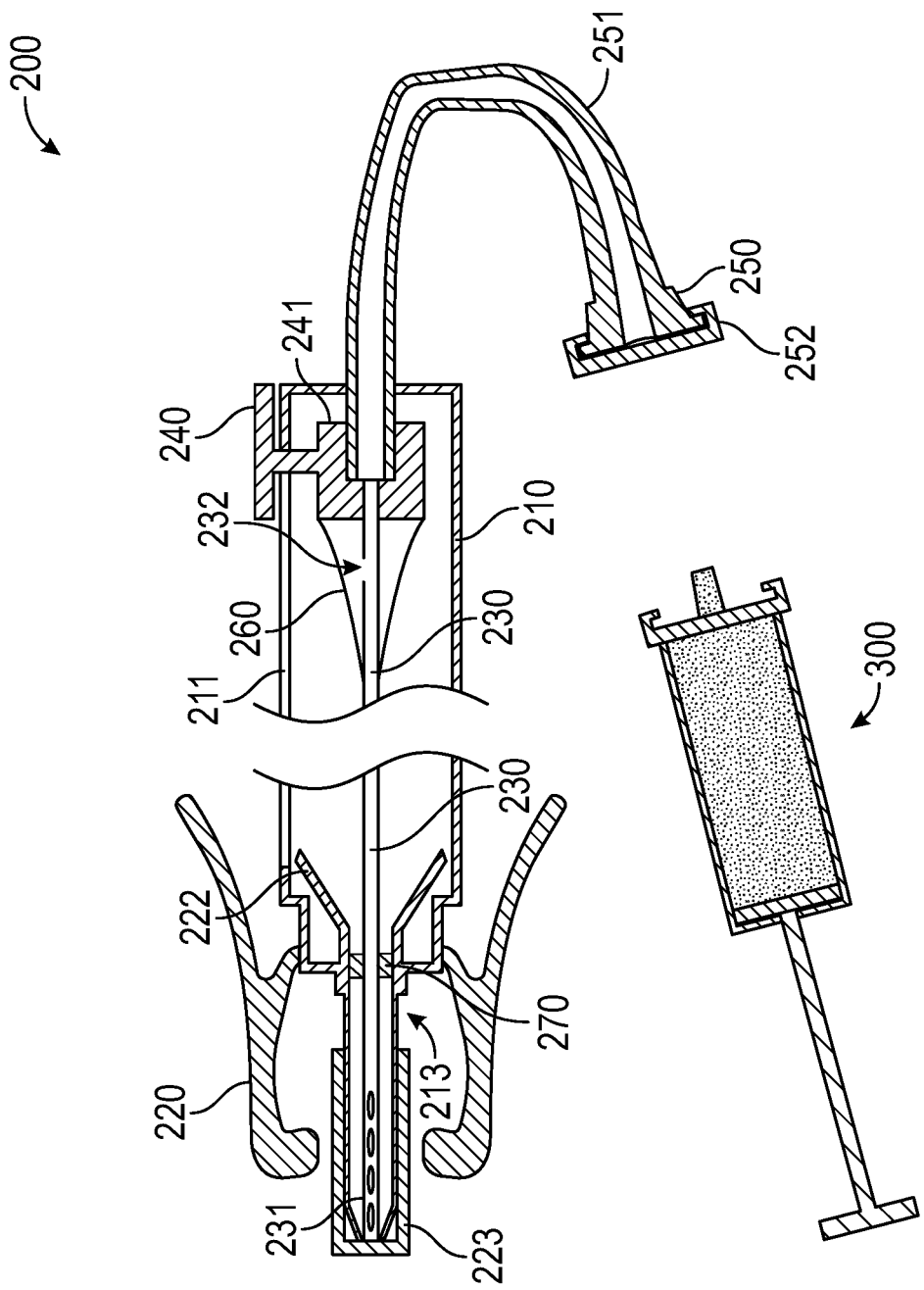
FIGS. 3A-3F represent one example of how the probe assembly of FIG. 2 may be used.

FIGS. 3A-3E provide an example of how probe assembly 200 may be used. In FIG. 3A, probe assembly 200 is represented in a pre-use state in which a cap 223 may be positioned overtop distal end 213 of probe housing 210, a cap 252 may be positioned overtop access port 250 and fluid container 260 may be empty. In some embodiments, probe assembly 200 may be packaged for distribution in this pre-use state. FIG. 3A also depicts a syringe 300 that contains a flushing fluid (e.g., saline). FIG. 3A may therefore represent a scenario where a clinician has inserted (or intends to insert) catheter 111 into a patient's vasculature but has not yet attached probe assembly 200 to catheter adapter 110.

Figure 3B:
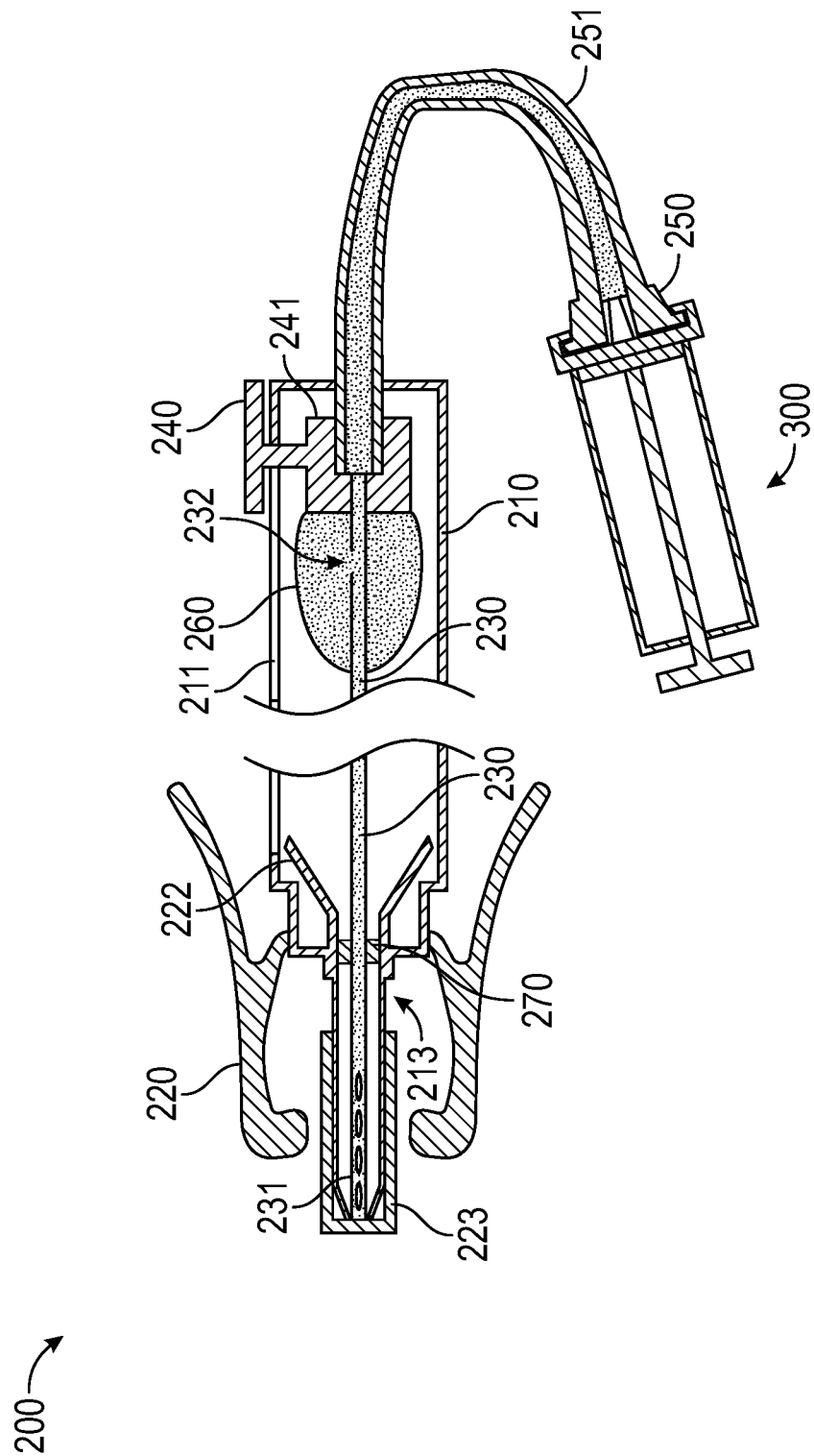

Turning to FIG. 3B, it is assumed that the clinician has removed cap 252 from access port 250 and attached syringe 300 to access port 250 to inject the flushing fluid into extension tubing 251. In this example, it is assumed that the clinician did not remove cap 223 from distal end 213 of probe housing 210 prior to injecting the flushing fluid. However, cap 223 could be removed at this stage. In any case, as the clinician injects the flushing fluid from syringe 300, the flushing fluid will flow into probe 230 and out through opening 232 to thereby fill fluid container 260 with the flushing fluid. The flushing fluid may also flow distally through probe 230 to thereby fill probe 230. Although not shown, probe assembly 200 may be configured to vent air from within probe 230 to allow the flushing fluid to fully fill probe 230. Accordingly, FIG. 3B may represent a step of priming probe assembly 200.

Figure 3C:
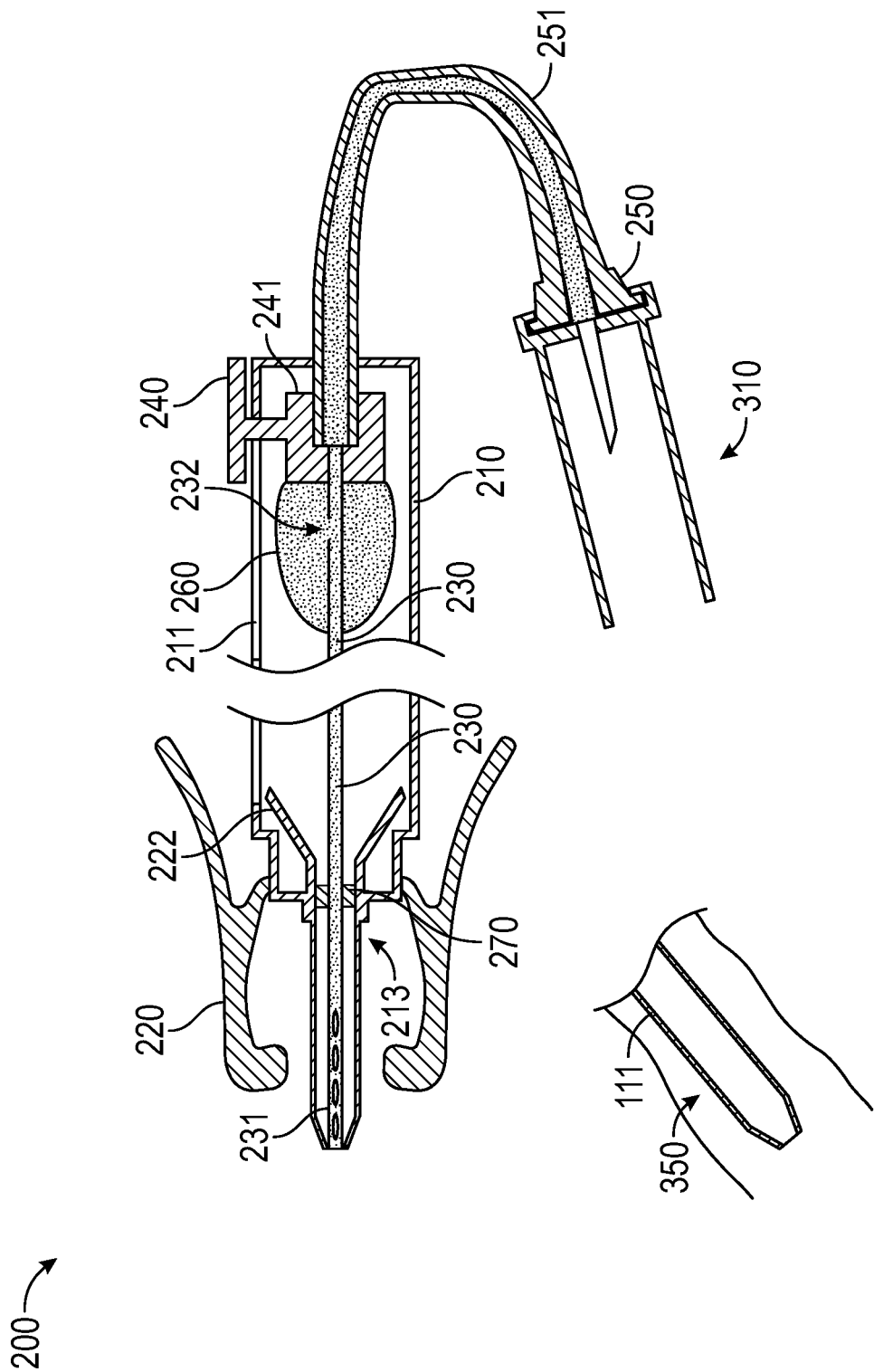

Turning to FIG. 3C, it is assumed that the clinician has detached syringe 300 from access port 250 and attached a blood collection set 310. It is also assumed that the clinician has removed cap 223 from distal end 213 of probe housing 210 in preparation for connecting probe housing 200 to catheter adapter 110. FIG. 3C further represents that catheter 111 has been inserted into the patient's vasculature 350.

Figure 3D:
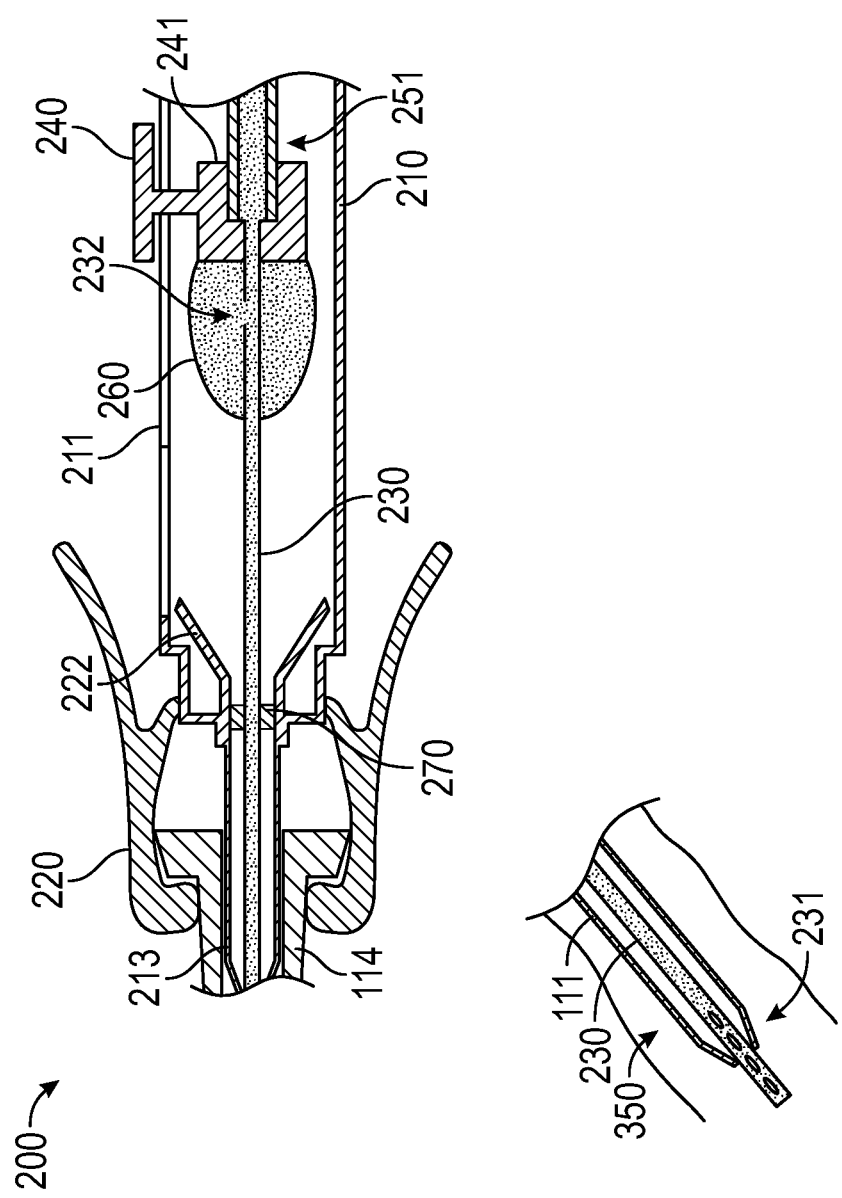

Turning to FIG. 3D, it is assumed that the clinician has connected probe assembly 200 to catheter adapter 110 via adapter 114 and has commenced sliding probe actuator 240 in a distal direction. Accordingly, fluid container 260 is shown as approaching compressing structure 222 as probe 230 approaches or begins to extend distally from catheter 111. With blood collection set 310 connected to access port 250, the flushing fluid will be held within probe 230 at this step of the process.

Figure 3E:
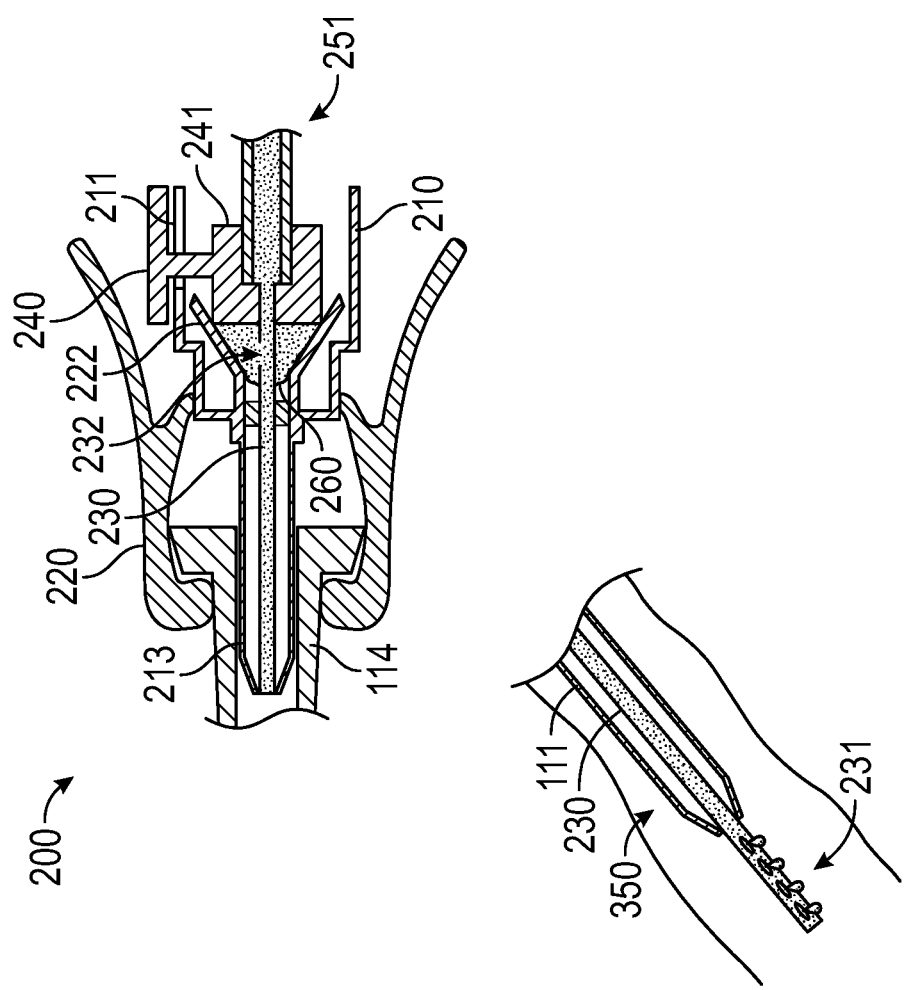

Turning to FIG. 3E, it is assumed that the clinician has slid probe actuator 240 fully into the distal-most position to thereby cause fluid container 260 to be compressed between compressing structure 222 and actuator body 241. The compression of fluid container 260 increases the fluid pressure within probe 230 thereby causing the flushing fluid to commence flowing out through fluid permeable structure 231 and into the patient's vasculature 350 (and possibly into catheter 111 if a portion of fluid permeable structure 231 is within catheter 111). The volume of fluid container 260 can enable a sufficient amount of flushing fluid to flow through fluid permeable structure 231 to prevent the formation of an occlusion around fluid permeable structure 231 as probe 230 is advanced fully into the patient's vasculature 350 or to otherwise remove an occlusion that may exist.

Figure 3F:
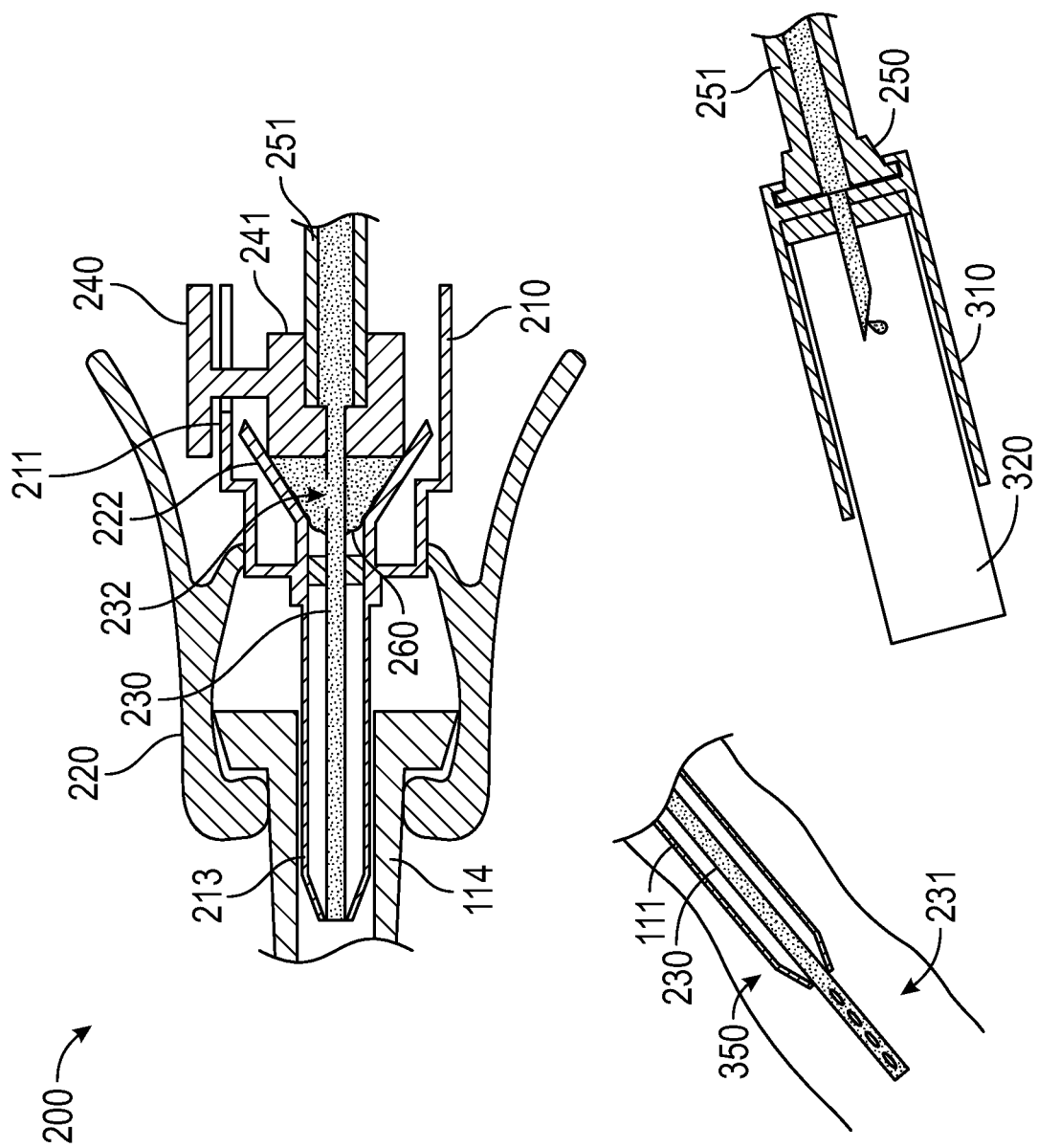

Finally, turning to FIG. 3F, after the flushing fluid has been injected through fluid permeable structure 231 to clear any occlusion that may exist, a vacuum tube 320 may be connected to blood collection set 310 to collect a blood sample. In such a case, the blood may flow into probe 230 via fluid permeable structure 231, then into extension tubing 251 and ultimately into vacuum tube 320. Any flushing fluid that may remain within probe 230 when the blood sample is collected may be drawn into a waste tube, may be held outside of the fluid path by a one-way valve, or may be isolated from the blood sample using any other suitable technique.

FIGS. 4 and 4A provide cross-sectional views of probe assembly 200 with another configuration of the integrated fluid flushing mechanism. In these figures, fluid container 260 is positioned immediately adjacent to compressing structure 222 (or, in the depicted embodiment, between the outwardly angled surfaces). Opening 232 can likewise be positioned towards the distal end of probe 230 so that it is within or otherwise fluidly coupled to fluid container 260. In such cases, actuator body 241 may have a similar configuration and perform a similar function as described above. In particular, as probe actuator 240 is moved into the distal-most position, actuator body 241 can contact and compress fluid container 260 between compressing structure 222.

The configurations depicted in FIGS. 2-4A could also be employed when probe 260 does not have a lumen. For example, the probe may be positioned within a catheter and the flushing fluid may flow along the exterior of probe 260 within the catheter.

FIG. 5 is a cross-sectional view of probe assembly 200 with another configuration of the integrated fluid flushing mechanism. Unlike previously described embodiments, FIG. 5 represents embodiments where probe housing 210 is filled with flushing fluid as opposed to using fluid container 260. Such embodiments may be primarily useful when probe 230 does not have a lumen (e.g., when probe 230 is a guidewire as represented in FIGS. 1A-1C). However, such embodiments could also be used when probe 230 has a lumen (e.g., when probe 230 is configured as shown in FIGS. 2 and 2A).

In FIG. 5, probe actuator 240 includes actuator body 241 to which the proximal end of probe 230 is connected as well as a stopper 242 that is positioned proximal to actuator body 241. Stopper 242 extends across the interior of probe housing 210 and functions to push the flushing fluid contained therein out through distal end 213 of probe housing 210 as probe 230 is extended distally from catheter 111. In other words, the distal movement of probe actuator 240 causes both actuator housing 241 (and therefore probe 230) and stopper 242 to move distally.

FIG. 6 illustrates a variation of the configuration shown in FIG. 5. In FIG. 6, stopper 242 is not connected to probe actuator 240 but is part of a plunger that extends proximally from actuator housing 210. Therefore, the distal movement of probe actuator 240 will cause probe 230 to be advanced distally, but the flushing fluid contained in probe housing 210 will be ejected in response to stopper 242 being separately pushed by the plunger.

In FIGS. 5 and 6, probe assembly 200 is not shown as including extension tubing 251 or access port 250. However, in these embodiments, extension tubing 251 could be coupled to the interior of probe housing 210 in any suitable location and in any suitable manner. For example, extension tubing 251 could insert through probe housing 210 at or towards the proximal end, a middle portion or the distal end of probe housing 210 to thereby be in fluid communication with the interior of probe housing 210. In such cases, extension tubing 251 and access port 250 could be used to inject the flushing fluid into probe housing 210 and/or to obtain a blood sample once probe 230 has been extended through catheter 111.

Figure 7:
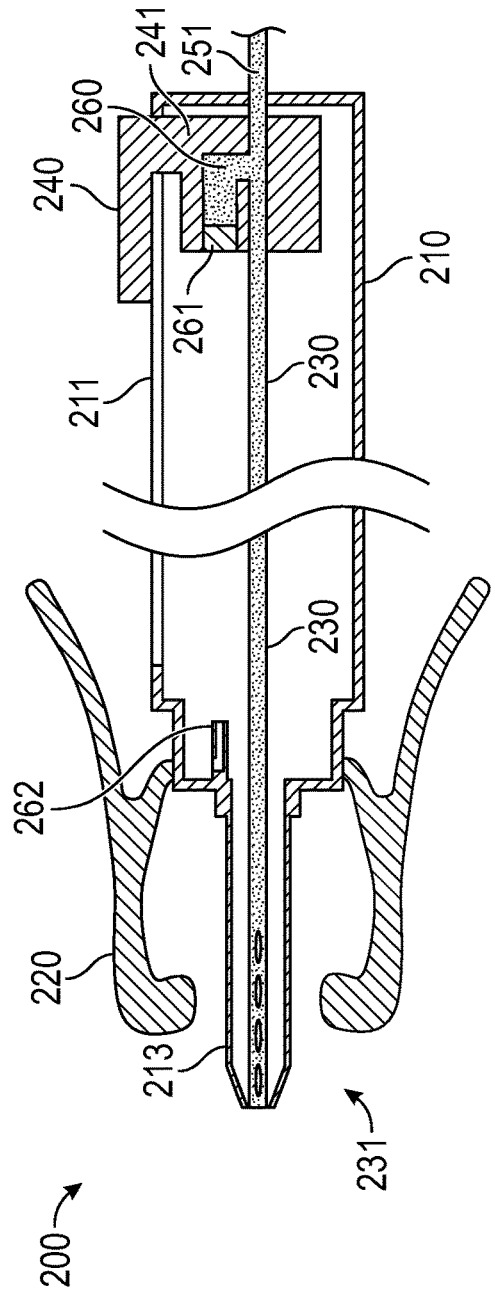
FIG. 7 is a cross-sectional view of a probe assembly that is configured in accordance with one or more embodiments.

FIG. 7 is a cross-sectional view of probe assembly 200 with another configuration of an integrated fluid flushing mechanism. As shown, actuator body 241 could itself form a fluid container 260 which need not be compressible. In such cases, a valve (or seal) 261 may be positioned in fluid container 260 and may be distally oriented. Valve 261 may function to retain the flushing fluid within fluid container 260. Probe housing 210 may also include a valve actuator 262 that is positioned towards distal end 213 of probe housing 210 and that is oriented proximally and aligned with valve 261. As probe actuator 240 is moved distally, valve 261 may be forced against valve actuator 262 which may pierce through valve 261 or otherwise create an opening therethrough which in turn will cause the flushing fluid in fluid container 260 to commence flowing through probe 230 and out through fluid permeable structure 231.

Figure 8:
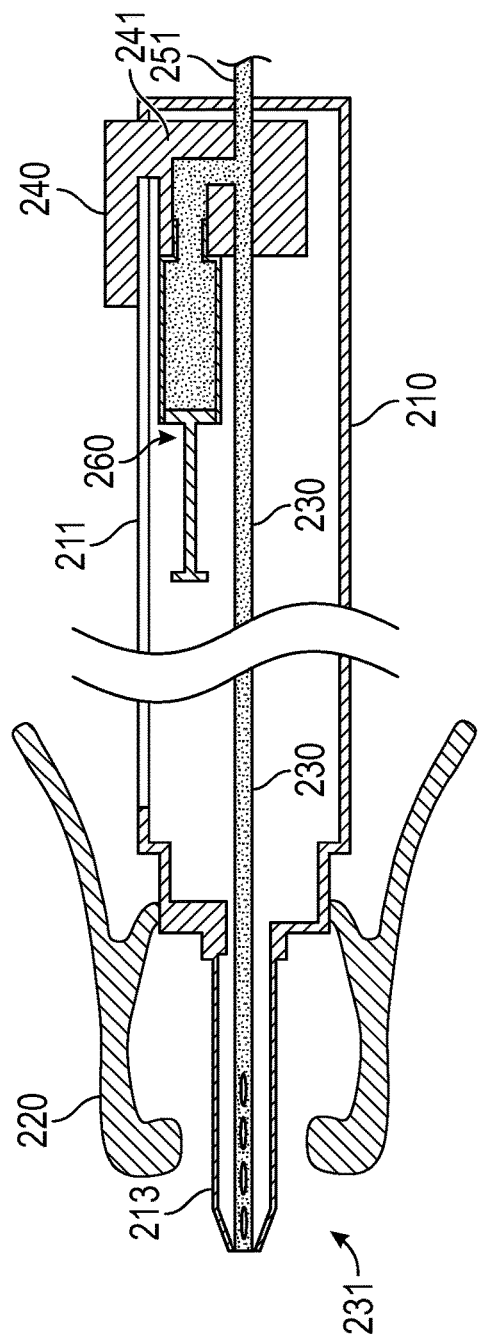
FIG. 8 is a cross-sectional view of a probe assembly that is configured in accordance with one or more embodiments.

FIG. 8 is a cross-sectional view of probe assembly 200 with another configuration of an integrated fluid flushing mechanism. In this configuration, fluid container 260 is in the form of a syringe that is fluidly coupled to actuator body 241 and therefore to probe 230 and extension tubing 251. This syringe also has its plunger distally oriented. Therefore, as probe actuator 240 is moved distally, the plunger of fluid container 260 will contact a distal sidewall of probe housing 210 thereby causing the flushing fluid contained in fluid container 260 to be injected through probe 230 and out through fluid permeable structure 231.

FIG. 9 is a cross-sectional view of probe assembly 200 with another configuration of an integrated flushing mechanism. In this configuration, probe housing 210 is configured to accommodate probe actuator 240 when it is in the form of a double-barreled plunger and to accommodate a probe tube 900*a* and probe tube branch 900*b*. Probe 230 is positioned within and slides along probe tube 900*a*. Probe tube branch 900*b* forms a fluid pathway between probe tube 900*a* and fluid container 260. In this configuration, fluid container 260 is positioned at a distal wall of probe housing 210.

Actuator body 241 is split into a first portion 241*a* and a second portion 241*b*. First portion 241*a* includes a channel 241*a*1 that is configured to receive probe tube 900*a* to thereby allow first portion 241*a* to slide along probe tube 900*a* to thereby advance probe 230 in a distal direction within probe tube 900*a*. Extension tubing 251 may extend into first portion 241*a* and may be in fluid communication with probe 230.

Second portion 241*b* is aligned with fluid container 260. Accordingly, as probe actuator 240 is moved in the distal direction to advance probe 230 distally from catheter 111, second portion 241*b* may contact and compress fluid container 260. The compression of fluid container 260 may cause the flushing fluid contained therein to flow through probe tube branch 900*b* and into probe tube 900*a*. Depending on the configuration of probe 230, this flushing fluid may either or both flow into probe 230 and around probe 230 to thereby cause the flushing fluid to pass through fluid permeable structure 231 as it is being extended distally out from catheter 111. In some embodiments, a valve 901 (e.g., a one-way valve) may be positioned in probe tune branch 900*b* to retain the flushing fluid within fluid container 260 until it is compressed and to prevent fluid (e.g., blood) from flowing back into fluid container 260.

FIG. 10 illustrates a variation of the configuration shown in FIG. 9. In this variation, fluid container 260 is in the form of a syringe having a plunger that is compressed by second portion 241*b*. In such embodiments, valve 901 may or may not be employed because the syringe may sufficiently retain the flushing fluid until the plunger is compressed and, once the plunger is compressed, the fluid pressure within probe tube 900*a* may be insufficient to force the plunger proximally.

Figure 11:
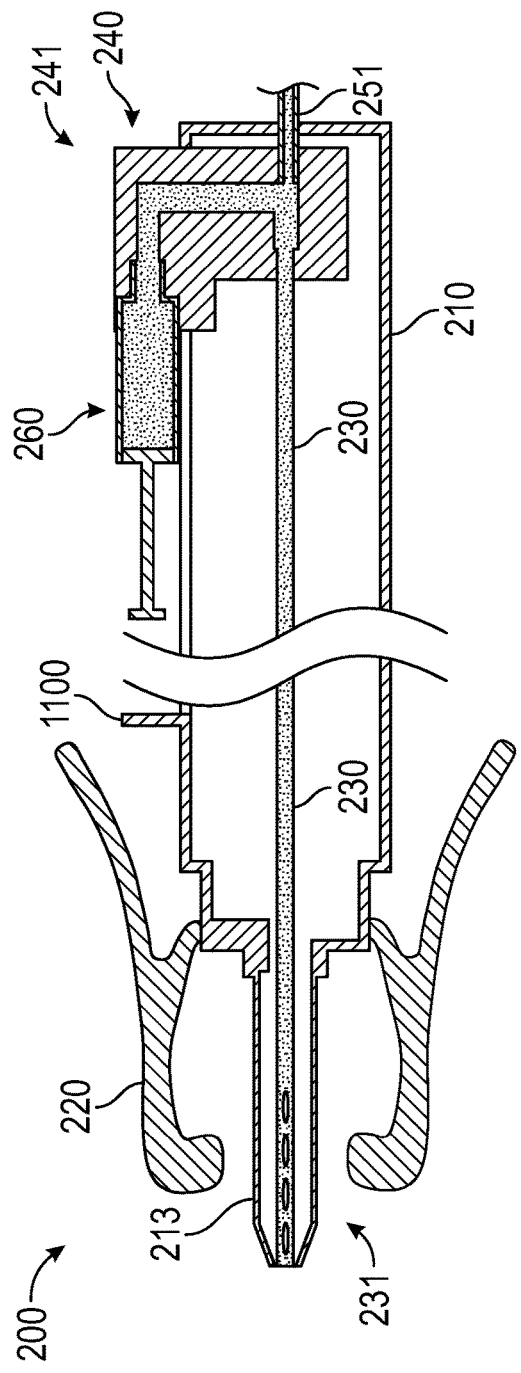
FIG. 11 is a cross-sectional view of a probe assembly that is configured in accordance with one or more embodiments.

FIG. 11 is a cross-sectional view of probe assembly 200 with another configuration of an integrated flushing mechanism. In this configuration, fluid container 260 is also in the form of a syringe, but it is positioned external to probe housing 210. In some embodiments, fluid container 260 may be pre-attached to probe actuator 240 or it may be attached by the clinician just prior to use. As such, actuator body 241 extends outwardly from probe housing 210 and provides a fluid pathway to probe 230. Probe housing 210 also includes an extension 1100 that is positioned distal to but in alignment with fluid container 260, or more particularly, with the plunger. Accordingly, as probe actuator 240 is slid distally, the plunger of fluid container 260 may be forced against extension 1100 thereby causing the flushing fluid in fluid container 260 to be injected into probe 230 and out through fluid permeable structure 231. Alternatively, a syringe may be attached to an access port (e.g., similar to access port 250 shown in FIG. 1A) for flushing during or after advancement of probe 230 prior to drawing blood.

Figure 12:
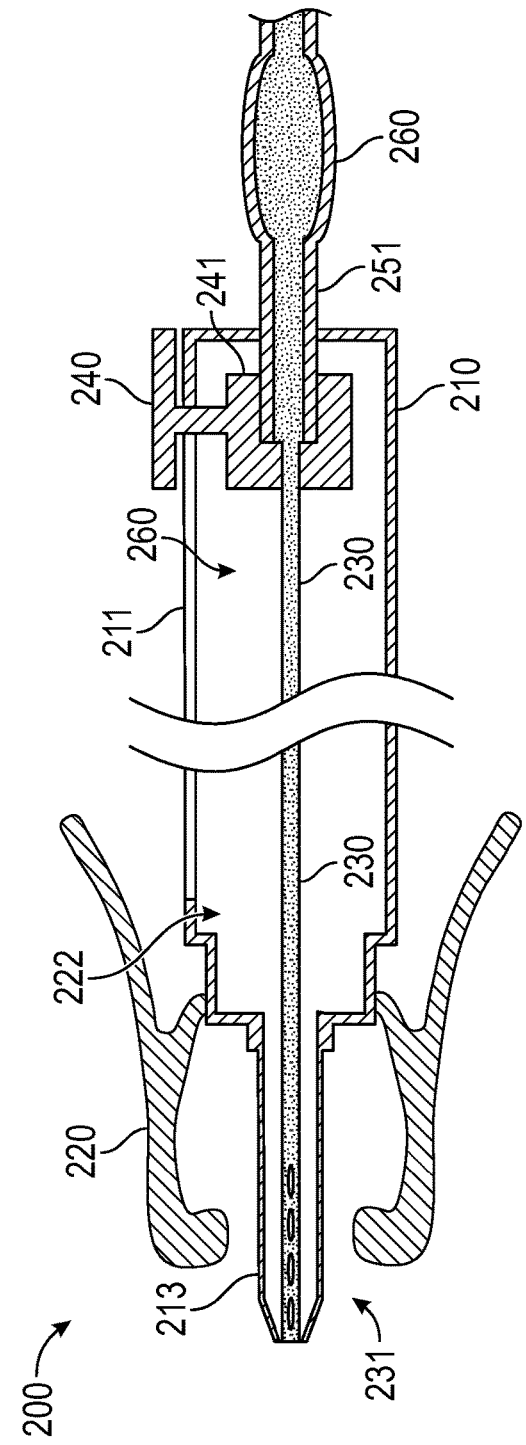
FIG. 12 is a cross-sectional view of a probe assembly that is configured in accordance with one or more embodiments.

FIG. 12 is a cross-sectional view of probe assembly 200 with another configuration of an integrated flushing mechanism. In this configuration, fluid container 260 is formed by a portion of extension tubing 251 that is configured to compress when it enters probe housing 210 or to otherwise be compressed (e.g., by manual compression). In the depicted configuration, as probe actuator 240 is slid distally, extension tubing 251 may be pulled into probe housing 210. As the portion of extension tubing 251 that forms fluid container 260 passes into probe housing 210, it may be compressed to thereby cause the fluid therein to be injected into probe 230 and out through fluid permeable structure 231. The position of fluid container 260 relative to probe housing 210 may be configured to cause the fluid to be injected through fluid permeable structure 231 as fluid permeable structure 231 extends from catheter 111.

In summary, a probe assembly may include an integrated fluid flushing mechanism that is configured in a wide variety of ways to cause the flushing fluid to be injected while the probe is being advanced distally out through a catheter and into a patient's vasculature. The probe of the probe assembly can include a fluid permeable structure through which the flushing fluid flows. The flushing fluid can prevent the formation of an occlusion and/or remove an occlusion that may have already formed around the fluid permeable structure. In this way, the fluid permeable structure of the probe will be enabled to perform its intended function of providing an unobstructed fluid pathway into or out of a catheter, including in scenarios where the catheter may have been in place in the patient's vasculature for extended periods of time.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A probe assembly comprising:
   a probe housing;
   a probe that extends within the housing, the probe having a fluid permeable structure at a distal end of the probe;
   a probe actuator that is configured to advance the probe from a proximal position to a distal position;
   an integrated fluid container that is integrated with the probe actuator, the integrated fluid container being configured to contain a flushing fluid and cause the flushing fluid to flow from the fluid container and through the fluid permeable structure while the fluid container moves distally relative to the probe housing and the probe is advanced to the distal position; and
   a compressing structure comprising an outwardly angled surface positioned so that the fluid container inserts into a space defined by the outwardly angled surface and compresses against the outwardly angled surface to expel the flushing fluid from the fluid container.

2. The probe assembly of claim 1, wherein the probe assembly is configured to couple to a catheter adapter from which a catheter extends, and wherein, when the probe is advanced to the distal position, the fluid permeable structure extends at least partially through a distal end of the catheter.

3. The probe assembly of claim 1, further comprising:
a probe tube within which the probe extends; and
a probe tube branch that connects the probe tube to the fluid container.

4. The probe assembly of claim 1, further comprising:
extension tubing that is fluidly coupled to the probe.

5. The probe assembly of claim 1, wherein the probe comprises a guidewire or a tube.

6. An intravenous (IV) catheter device comprising:
a catheter adapter from which a catheter extends distally; and
the probe assembly of claim 1, which is configured to couple to the catheter adapter.

7. A method for accessing a vasculature comprising:
coupling the probe assembly of claim 1 to a catheter adapter having a catheter that is inserted into a patient's vasculature; and
in conjunction with sliding the probe actuator in a distal direction to cause the fluid permeable structure of the probe to extend distally from the catheter, activating the integrated fluid container to thereby cause the flushing fluid contained in the fluid container to flow from the fluid container, into the probe, and through the fluid permeable structure as the fluid container moves distally relative to the probe housing and the fluid permeable structure advances distally from the catheter.

8. The method of claim 7, further comprising:
obtaining a blood sample via the probe assembly while the fluid permeable structure is advanced distally from the catheter.

9. The probe assembly of claim 1, wherein the integrated fluid container is connected to a distal side of the probe actuator.

10. The probe assembly of claim 1, wherein the outwardly angled surface is angled relative to a longitudinal axis of the probe housing, such that the space defined by the outwardly angled surface is a frustoconical space oriented with a wide end of the space positioned proximal to a narrow end of the space.

11. The probe assembly of claim 1, wherein the probe passes through the space defined by the outwardly angled surface.

12. The probe assembly of claim 1, wherein the fluid container is compressed between the probe actuator and the compressing structure.

* * * * *